United States Patent [19]

Steiner

[11] 4,397,046

[45] Aug. 9, 1983

[54] PROTECTING DEVICE ESPECIALLY FOR MOTOR-CYCLISTS

[75] Inventor: Michel Steiner, Geneva, Switzerland

[73] Assignee: Lacoray S.A., Geneva, Switzerland

[21] Appl. No.: 278,465

[22] Filed: Jun. 29, 1981

[51] Int. Cl.$^3$ .............................................. A61F 5/02
[52] U.S. Cl. ...................................................... 2/44
[58] Field of Search ....................... 2/2, 44, 45; 5/451

[56] References Cited

U.S. PATENT DOCUMENTS

| 1,532,037 | 3/1925 | Cahill . | |
| 2,255,464 | 9/1941 | Hall, Jr. | 2/44 |
| 2,973,030 | 2/1961 | Matthewson | 2/44 |
| 4,059,852 | 11/1977 | Crane . | |

FOREIGN PATENT DOCUMENTS

| 2717712 | 10/1978 | Fed. Rep. of Germany . |
| 2082495 | 12/1971 | France . |
| 2159561 | 6/1973 | France . |
| 2396521 | 2/1979 | France . |
| 1479733 | 7/1977 | United Kingdom . |

Primary Examiner—Doris L. Troutman
Attorney, Agent, or Firm—Young & Thompson

[57] ABSTRACT

The protecting device comprises a vertebral column protecting element (2) presenting at its higher end a nape protecting element (3) and at its lower end a belt (1), a tight chamber extending on these three elements and being provided with automatically releasable inflating means (10).

The protecting device can be beared as a harness by means of straps (15, 16) or incorporated to a clothing. It allows in case of accident to decrease the risks or the severity of injuries to the vertebral column, to the nape and to the lumbar region.

19 Claims, 6 Drawing Figures

PROTECTING DEVICE ESPECIALLY FOR MOTOR-CYCLISTS

The present invention relates to a protecting device especially for motor-cyclists.

It is known that there is now no appropriate protection for motor-cyclists, except the helmet, the protecting function thereof being limited to the head, and the pads with which some clothes for motor-cyclists are provided especially at the articulations (elbows, knees) and the protecting function of which is insufficient. It is also known completely inflatable clothes, which however present the drawback of leading to the rebounding of the user on the ground in case of fall, and thereby to the introduction of an additional risk of damages. As a matter of fact, the statistics show that most of accidents lead to severe or even permanent damages to the vertebral column which is not protected.

Consequently, the purpose of this invention is to remedy to that lack by providing a protecting device especially for motor-cyclists more particularly intended for protecting the vertebral column of the user, including the cervical vertebrae and eventually the lumbar region. This purpose is reached thanks to the device according to the invention, which is characterized by the fact that it comprises at least a tight chamber which is provided with automatically releasable inflating means and is presenting fixing means intended for cooperating in service position with the body of the user and in such a manner that said chamber be disposed at least along the vertebral column and the nape of said user.

The protecting device according to the invention will be now described in more details in reference to the annexed drawing which illustrates schematically and by way of examples two particular realizations.

Figure 1:
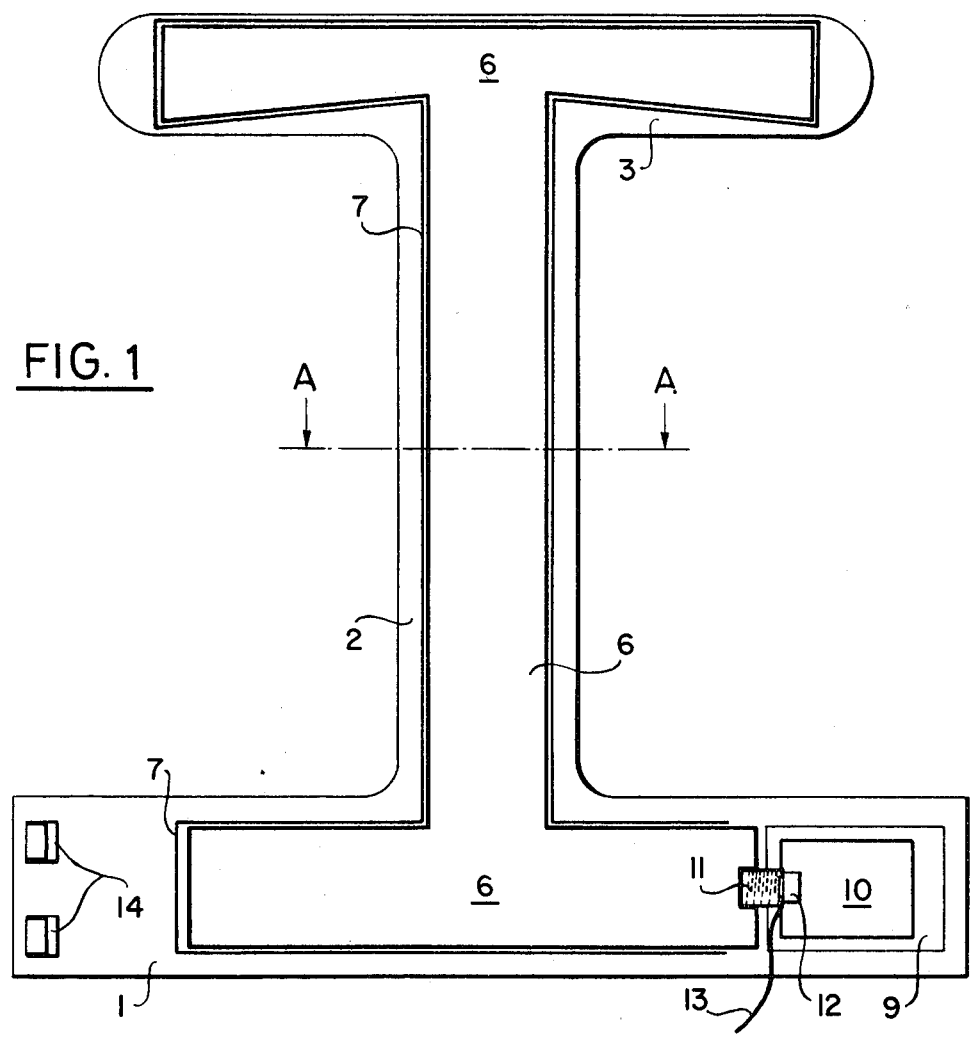
FIG. 1 is a plan view of a first embodiment of the device according to the invention.
Figure 2A:
FIGS. 2A and 2B are cross-section views according to the line AA of FIG. 1, respectively in normal and in inflated position.
Figure 2B:
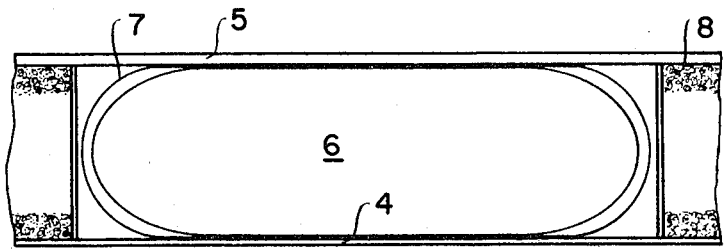

In reference at first to FIGS. 1, 2A and 2B, the device according to the invention as illustrated comprises three elements joined the one with the other, respectively a belt 1, a vertebral column protecting element 2 and a nape protecting element 3, the belt 1 and the nape protecting element 3 being each disposed perpendicularly to one of the ends of the column protecting element 2. The above three elements can be, as illustrated on FIG. 1, made of one piece, or can be separately realized and provided with means for assembling them together in an appropriate manner.

As shown on FIGS. 2A and 2B, the three elements are preferably constituted of two superimposed layers made of leather, or of synthetic material presenting similar properties, the internal layer 4 being fine and soft whereas the external layer 5 being more thick and more rigid.

Between both precited layers an air tube is disposed, for example made of rubber or of an elastic plastic material, generally encompassed by a sheath 7 for exemple of an elastic textile material. The internal faces of both superimposed layers 4, 5 can be provided, on each side of the air tube 6, with a bounding strip 8 of the type "Velcro" maintaining said layers the one against the other in the normal deflated position (FIG. 2A).

With regards to the sizes of the device shown on FIG. 1, it is to be noted that the length of the column protecting element 2 depends on the size of the user and should be realized so as to go from the nape to the lumbar region of said user, that is to the place for the belt. The width of the air tube 6 is generally of about 15 cm at least for the parts forming the belt 1 and the column protecting element 2 and rather less for the part forming the nape protecting element 3.

The belt 1 comprises near one of its ends a pocket 9 containing a cartridge 10 of compressed gas, for exemple of air, carbonic gas, or of any gaseous mixture appropriated for being easily kept at compressed state and for being quickly expanded when necessary. This cartridge is removably connected to an intake nozzle with which the air tube 6 is provided by means of a fixing device 11 of a known type such as a screw threated, bayonet or clips device. The cartridge 10 is further provided with automatic releasing means, for example comprising a split spin 12 controlling the opening of said cartridge 10, said split spin 12 being connected to a control thread or wire 13, the use of which will be explained thereafter.

Furthermore, the belt 1 is provided at its ends with locking means 14 of any known type.

Figures 3A, 3B:
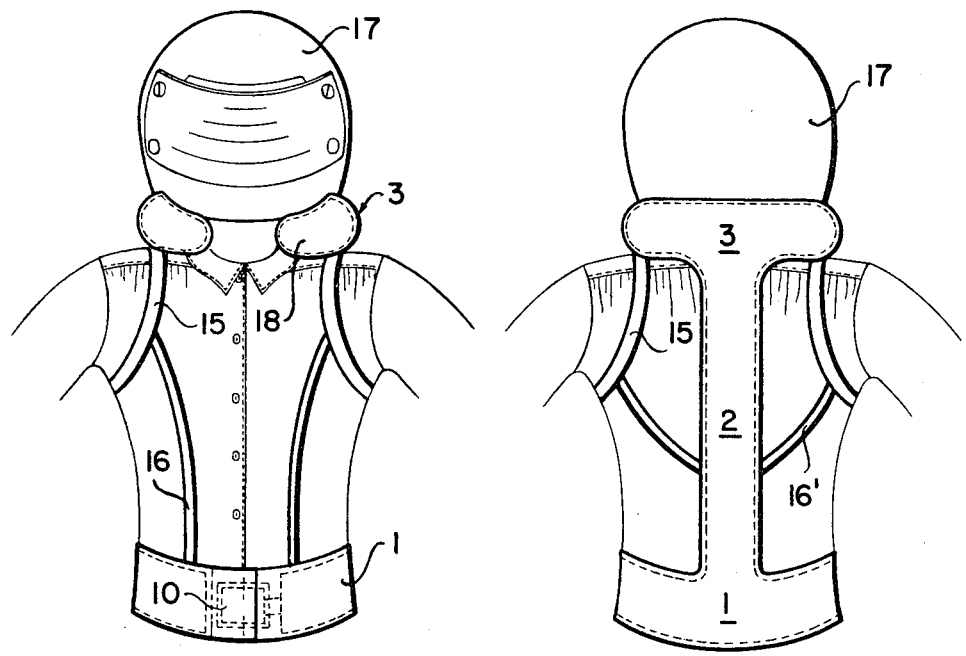
FIGS. 3A and 3B are respectively face and back views of the embodiment of FIG. 1 beared by a motor-cyclist as a harness.

As illustrated on FIGS. 3A and 3B, the protecting device according to the invention as described in reference to FIG. 1 is intended to be attached for example on a motor-cyclist as a harness. It comprises thus two straps 15 fixed near the ends of the nape protecting element 3 and forming two loops passing under the armpits of the motor-cyclist. In order to ensure the keeping in position of the device on the body of the motor-cyclist, the straps 15 can be binded before to the belt 1 (FIG. 3A) and behind to the column protecting element 2 (FIG. 3B) by means of other straps respectively 16 and 16'.

The column protecting element 2 is thus disposed along the vertebral column of the motor-cyclist and the nape protecting element 3 on the nape of said user, at the limit of the helmet 17, the belt 1 being locked in a usual way and in such a manner that the lower part of the air tube 6 is disposed on the lumbar region of the motor-cyclist and that the compressed gas cartridge 10 is placed in the ventral region of said user. Finally, the nape protecting element 3 preferably presents extensions 18 (FIG. 3A) which are disposed laterally and around the neck of the user until under his jaw so as to protect it.

Figure 4:
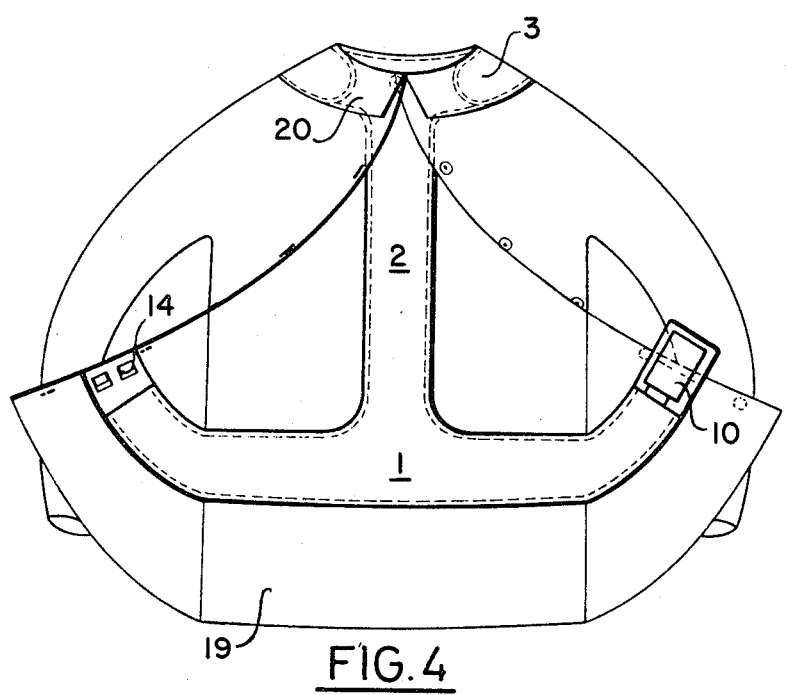
FIG. 4 is a view of a second embodiment of the device according to the invention under the form of a protecting clothing especially for motor-cyclist.

According to a second embodiment shown on FIG. 4, the protecting device according to the invention can be incorporated or attached in a removable manner to a clothing.

More particularly, the protecting device can be attached, by sewing it, during the making up of a clothing 19 such a jacket, a lumber-jacket, a wind-breaker, or a one-piece unit, between the internal lining and the external skin or fabric. According to a variant, the protecting device can comprise means such as buttons, snap-fasteners, clips, or bands of the type "Velcro" enabling to attach it in a removable manner to corresponding means with which the inside of the clothing 19 is provided.

The protecting belt 1 of the device can also be used for the locking of the clothing itself. With regards to the nape protecting element 3, it is preferably incorporated to the collar 20 of the clothing 19 so to be able to be lifted onto the nape of the user when the air tube contained in it is in inflated position.

As soon as the protecting device according to the invention is sufficiently firmly attached for example on a motor-cyclist, either by means of appropriated straps or by the locking of the protecting clothing, so as it cannot be displaced by the movements of the motor-cyclist, it is thus in the normal service position. When he takes place onto his motor-cycle, the motor-cyclist should attach the free end of the control thread of wire 13, connected to the releasing split spin 12 of the compressed gas cartridge 10, to a fixed part of the motor-cycle, said free end being therefore provided with a hook or any other element able to be attached to the motor-cycle.

In case of accident or fall, the ejection of the motor-cyclist with regards to the motor-cycle leads to the wrench of the split spin 12, this latter remaining bound to the motor-cycle by the control wire 13, and releases the introduction of the gas contained within the cartridge 10 into the air tube 6 leading immediately to the inflating thereof. The motor-cyclist is thus protected by the presence of air cushions disposed along his vertebral column, on his nape and eventually on his lombar region. As illustrated on FIG. 2B, the external layer 5 of the device is relatively thick and rigid, this reinforcing further the protection property thereof in case of shocks or crushing, the soft and fine internal layer 4 conforming itself to the morphology of the motor-cyclist.

Of course, other not shown variants of both embodiments of the protecting device according to the invention described by reference to the annexed drawing are possible. For example, the inflatable tight chamber of the device can be constituted by several air tubes or chambers each completely independent and each provided with their own automatically releasable inflating means or by several air tubes or chambers connected the ones with the others and being inflatable from a sole automatically releasable inflating device.

The disposition and the form of the compressed gas cartridge(s), as well as the number thereof, are not limited. Furthermore, the automatic releasing of the opening of the compressed gas cartridge for the instantaneous inflating of the air tube(s) can be different from those described above by way of example. As a matter of fact, control devices are known for the discharge of a compressed gas cartridge which react for example to a sudden decceleration or to a shock and which can be eventually be used here.

According to another not shown variant, the nape protecting element can be combined with an additional element which is lifted by inflating behind the user's head until above said head or which takes the form of a kind of helmet.

Finally, in the case of the protecting garment according to the invention, it can be also provided with other tight chambers with automatically releasable inflating means, for example of the articulations (knees, elbows).

The device according to the invention thus constitutes a protection for example for the motor-cyclist who had not until now at his disposal. This device is simple and relatively cheap and allows to decrease in an important manner the risks of severe or even permanent injuries or organs such as the vertebral column, the cervical vertebrae and eventually the lumbar region, especially in case of fall or motor-cycle accident.

Of course, the device or clothing according to the invention can be intended for the protection not only of the motor-cyclists, but also of the drivers and passengers of side-cars, and of any person practising a sport or any other motorized or not motorized activity which presents risks of accidents leading to injuries to the vertebral column, the nape and/or the lombar region.

While the invention has been described in detail and with reference to specific embodiments thereof, it will be apparent to one skilled in the art that various changes and modifications can be made therein without departing from the spirit and scope thereof.

What is claimed is:

1. Protecting device especially for motor-cyclists comprising at least a tight chamber which is provided with automatically releasable inflating means and is presenting fixing means intended for cooperating in service position with the body of the user and in such a manner that said chamber is disposed at least along the vertebral column and the nape of said user.

2. Device according to claim 1 comprising a vertebral column protecting element presenting a nape protecting element at its higher end and a belt at its lower end.

3. Device according to claim 2 in which a sole inflatable chamber extends on the three elements.

4. Device according to claim 1 comprising several independent chambers each being provided with automatically releasable inflating means.

5. Device according to claim 1 comprising several chambers connected the ones with the others and with a sole automatically releasable inflating device.

6. Device according to claim 1 in which the inflating means comprise a compressed gas cartridge provided with fixing means cooperating with corresponding fixing means with which a gas intake element of the chamber is provided, said cartridge being further connected to an automatic opening control device.

7. Device according to claim 6 in which the automatic control device of the opening of the compressed gas cartridge comprises a split pin connected to a control thread or wire intended to be attached to an element independent from the user.

8. Device according to claim 6 in which the cartridge is attached near one of the ends of the belt, in order to be in service position on the ventral region of the user.

9. Device according to claim 1 in which the tight chamber is constituted by an air tube made of an elastic material, and is disposed between two layers of leather or synthetic material, the external layer being more thick and more rigid than the internal layer.

10. Device according to claim 1 which is provided with straps intended for the fixation thereof in service position on a user in such a manner that the inflatable chamber extends at least along his vertebral column and on his nape.

11. Protecting clothing especially for motor-cyclists, comprising a protecting device incorporated within its internal lining or attached to it in a removable manner, said protecting device comprising at least a tight chamber which is provided with automatically releasable inflating means and is presenting fixing means intended for cooperating in service position with the body of the user and in such a manner that said chamber be disposed at least along the vertebral column and the nape of said user.

12. Protecting clothing according to claim 11 in which said device comprises a vertebral column protecting element presenting a nape protecting element at its higher end and a belt at its lower end.

13. Protecting clothing according to claim 12 in which a sole inflatable chamber extends on the three elements.

14. Protecting clothing according to claim 11 in which said device comprises several independent chambers each being provided with automatically releasable inflating means.

15. Protecting clothing according to claim 11 in which said device comprises several chambers connected the ones with the others and with a sole automatically releasable inflating device.

16. Protecting clothing according to claim 11 in which the inflating means of the protecting device comprise a compressed gas cartridge provided with fixing means cooperating with corresponding fixing means with which a gas intake element of the chamber is provided, said cartridge being further connected to an automatic opening control device.

17. Protecting clothing according to claim 16 in which the automatic control device of the opening of the compressed gas cartridge comprises a split spin connected to a control thread or wire intended to be attached to an element independent from the user.

18. Protecting clothing according to claim 16 in which the cartridge is attached near one of the ends of the belt, in order to be in service position on the ventral region of the user.

19. Protecting clothing according to claim 11 in which the tight chamber of the protecting device is constituted by an air tube made of an elastic material, and is disposed between two layers of leather or of synthetic material, the external layer being more thick and more rigid than the internal layer.

* * * * *